United States Patent [19]
Zuehlsdorff

[11] 3,989,035
[45] Nov. 2, 1976

[54] DISPOSABLE MEDICAL ELECTRODE
[75] Inventor: Werner G. Zuehlsdorff, La Crescenta, Calif.
[73] Assignee: Stemmen Laboratory, Inc., Costa Mesa, Calif.
[22] Filed: Aug. 4, 1975
[21] Appl. No.: 603,026

[52] U.S. Cl. .......................... 128/2.1 E; 128/417; 128/DIG. 4
[51] Int. Cl.² .......................................... A61B 5/04
[58] Field of Search .......... 128/2.06 E, 2.1 E, 404, 128/410, 411, 417, 418, DIG. 4

[56] References Cited
UNITED STATES PATENTS

| | | | |
|---|---|---|---|
| 3,587,565 | 6/1971 | Tatoian | 128/2.06 E |
| 3,677,268 | 7/1972 | Reeves | 128/417 |
| 3,701,346 | 10/1972 | Patrick et al. | 128/2.06 E |
| 3,750,094 | 7/1973 | Zenkich | 128/2.06 E |
| 3,805,769 | 4/1974 | Sessions | 128/2.06 E |
| 3,828,766 | 8/1974 | Krasnow | 128/2.1 E |
| 3,830,229 | 8/1974 | Johnson | 128/2.06 E |
| 3,834,373 | 9/1974 | Sato | 128/2.06 E |
| 3,841,312 | 10/1974 | Corasanti | 128/2.1 E |
| 3,868,946 | 3/1975 | Hurley | 128/2.1 E |
| 3,901,218 | 8/1975 | Buchalter | 128/2.06 E |

Primary Examiner—Robert W. Michell
Assistant Examiner—Lee S. Cohen
Attorney, Agent, or Firm—Knobbe, Martens, Olson, Hubbard & Bear

[57] ABSTRACT

An electrode for attachment to the skin includes an electrode body of flexible sheet material coated with adhesive for attachment to the skin and manufactured of either liquid absorbent or liquid impervious material. Attached to this flexible sheet by a male snap fastener member is a liquid vapor barrier sheet which is likewise coated with adhesive for adhesion to a liquid absorbent sponge member which is filled with electrolyte. A thin, moisture impervious carrier sheet is attached to the adhesive coating on both the moisture impervious sheet and the flexible body and is additionally attached, through a heat sealing process, to a cup member which prohibits evaporation or migration of the electrolyte from the liquid absorbent sponge member prior to use. A soft, flexible, annular sealing member may be attached to the moisture and liquid vapor barrier sheet to surround the electrolyte-filled sponge member during use to prohibit migration of electrolyte between the adhesive coated sheet and the patient's skin. This construction results in a long shelf life electrode which may be effectively used on a patient for extended periods of time.

14 Claims, 7 Drawing Figures

DISPOSABLE MEDICAL ELECTRODE

BACKGROUND OF THE INVENTION

The present invention relates to medical electrodes used for monitoring electrical signals from the skin of a patient and more particularly to disposable electrodes which are prepackaged in a condition ready for use.

Numerous attempts have been made in the prior art to produce a satisfactory disposable medical electrode which would exhibit the electrical characteristics necessary for a low noise signal from the skin of a patient, comfort to the patient during long-term usage, and long shelf life prior to use. In many instances these requirements contradict one another, such that the prior art has achieved success in meeting one requirement only at the expense of another. Thus, for example, long shelf life might be insured by utilizing additional packaging materials. Similarly, the reduction of spurious noise signals, commonly termed motion artifacts, is typically accomplished only at the expense of discomfort to the patient.

As in the case of any disposable item, low cost is an important factor in the design of such electrodes. The prior art electrodes have required the use of multiple packaging techniques in order to insure long shelf life. Thus, the prior art electrode packages typically have included both a protective cover member over the electrolyte and an outer foil container over the entire electrode. This outer foil container has heretofore been necessary for achieving a reasonable shelf life for a pre-gelled electrode. Such packaging necessarily increases the cost of each of the electrodes and, particularly in instances where multiple electrodes are contained in a single foil package, the use of one of the included electrodes subjects the remaining electrodes to evaporation of electrolyte and a resulting requirement that they be used promptly.

The prior art also exhibits the use of barriers to prevent migration or evaporation of electrolyte from the central conductive portion of the electrode to the surrounding area where the electrode is adhesively attached to the patient. These barriers are commonly constructed of rigid material, and are thus subject to being lifted from the skin of the patient when the patient moves, reducing the effectiveness of the moisture barrier, and are uncomfortable to use due to the rigid surface pressed against the patient's skin.

Even in those prior art medical electrodes which sacrifice other characteristics in an effort to provide long shelf life, significant evaporation and migration of electrolyte typically occurs between the cup member used to cover the electrolyte-filled foam member and the carrier sheet to which the cup member has been attached. This migration and evaporation is due primarily to the use of a paper carrier sheet and a simple adhesive attachment to the cup member to this sheet, both of which subject the electrode to electrolyte loss.

SUMMARY OF THE INVENTION

The present invention provides a medical electrode which reduces motion artifacts, has virtually indefinite shelf life without using multiple packaging techniques, is comfortable for the patient to wear during extended periods of time and is relatively inexpensive. Each of these characteristics is achieved in the electrode of the present invention without compromise to the remaining requirements. This is accomplished through the use of particular materials and construction processes as well as the structure of the electrode which is described below.

Generally, the electrode of the present invention includes an electrode body which is designed to be attached directly to the skin of the patient. This body is constructed of liquid absorbent or liquid impervious adhesive coated flexible sheet material and is attached to a liquid vapor barrier sheet underlying the body and having a smaller perimeter than the body by a conductive, metallic, male snap fastener formed of two pieces which are swaged together around the adhesive body sheet and liquid vapor barrier sheet to permanently attach these elements. The liquid vapor barrier sheet is additionally attached to the adhesive body sheet by the adhesive backing on the latter sheet. This liquid vapor barrier sheet prohibits evaporation or migration of electrolyte material through the adhesive body during storage and use of the medical electrodes. The liquid vapor barrier sheet is also coated with adhesive material on one or both sides, but at least on the surface opposite the adhesive body. If the surface adjacent the adhesive body is coated with adhesive, this adhesive will tend to increase the separation resistance of the adhesive body and liquid vapor barrier sheet.

A liquid absorbent sponge member is attached to the adhesive surface of the liquid vapor barrier sheet opposite the adhesive body and is filled with electrolyte of a commercially available variety, typically in the form of a paste or gel. The electrolyte within this sponge member assures conduction of electricity between the snap fastener and the patient's skin and determines the area of electrical contact between the medical electrode and the skin of the patient. The electrode is manufactured with the electrolyte already impregnated within the sponge member, although the sponge member is conveniently attached to the adhesive on the moisture impervious sheet prior to impregnation with electrolyte to assure that the electrolyte does not interfere with this adhesion.

The sponge member has a smaller perimeter than the liquid vapor barrier sheet so that the perimeter of the liquid vapor barrier sheet is left exposed after application of the sponge member. This perimeter area, and the adhesive coating thereon, is used to attach the electrode to a carrier sheet which is thin and flexible and advantageously formed of KIMDURA material. This material has excellent moisture proofing characteristics and assures the integrity of the seal for the electrolyte during storage. The upper surface of the carrier sheet is also attached to the adhesive body member by the adhesive coating on the latter element. When the electrode is to be used, the adhesive coated body, together with the liquid vapor barrier sheet, sponge member and snap fastener, is removed from the carrier sheet. It is important that the adhesive on the body member and liquid vapor barrier sheet not be damaged during this removal, and that the removal be accomplished without tearing the body member. In order to facilitate such removal, the upper surface of the carrier member is conveniently coated with silicon which, while allowing a limited degree of adhesion between the adhesive substances and the carrier sheet, still permits ready removal of these members.

The surface of the carrier sheet opposite the body member and liquid vapor barrier sheet is coated with a heat sealing composition which will melt upon the application of a predetermined temperature. A cup member, also formed of heat sealable material, covers the sponge member opposite the snap fastener and is attached by heat sealing to the carrier member to provide a moisture impervious container for the electrolyte-impregnated sponge element. The sponge element, with its enclosed electrolyte, is therefore separated from ambient conditions during storage by a interface of the snap fastener, the liquid vapor barrier sheet, the carrier sheet, and the cup member, each of which has excellent moisture and vapor impervious characteristics, and each of which is bonded together in a manner which prevents evaporation or migration of the electrolyte between the elements. As a result, electrodes constructed in accordance with this invention have a very long shelf life without the use of any outer foil container.

A second embodiment of the present invention includes, in addition to the elements described above, a resilient, flexible, annular ring attached to the liquid vapor barrier sheet surrounding the sponge member. This ring enhances the usefulness of the electrode during extended application to a patient, since it confines the electrolyte to an area within the annular ring by resiliently sealing against the patient's skin. The resilience of this element enhances its sealing characteristics to the skin and makes the electrode comfortable during use, since it has no hard surfaces that press into the patient's skin or rub against bony areas of the patient's body. Adhesion of the adhesive pad member and the liquid vapor barrier sheet to the patient's skin assures a resilient bond between the annular sealing ring and the patient's skin. In addition, the annular ring may include an adhesive layer to bond its surface, opposite the liquid vapor barrier sheet, to the patient's skin.

BRIEF DESCRIPTION OF THE DRAWINGS

The present invention is best understood through the following detailed description and the drawings, in which.

DESCRIPTION OF THE PREFERRED EMBODIMENT

Referring initially to FIGS. 1, 3, 4 and 6, a first embodiment of the present invention will be described. A circular adhesive coated member 11 is in the shape of a disc and forms the main body of the medical electrode 13. This disc may be formed from any material suitable for electrode manufacture, examples being a foamed plastic material such as polyurethane or polyethylene, a paper tape such as the tape marketed by 3M Co. under the trademark MICROPORE, or a cloth tape such as the tape marked by Johnson & Johnson Co. under the trademark DERMICIL. This body member 11 is relatively flexible and may be made of either liquid absorbent or liquid impervious material. It will be recognized by those skilled in the art that liquid absorbent material may make the electrode 13 more comfortable to wear for extended periods of time, since the body member 11 will be free to breathe to some extent and thus allow air to ventilate the skin area covered by the adhesive pad 11. Both the abovementioned paper and cloth tape materials are highly porous and therefore permit ventilation of the skin. As is well known in the art, member 11 is preferably quite flexible, so that it may conform to the curvatures of the skin thereby maintaining a more cohesive contact without pulling either away at the edges or causing discomfort to the patient.

Figure 6:
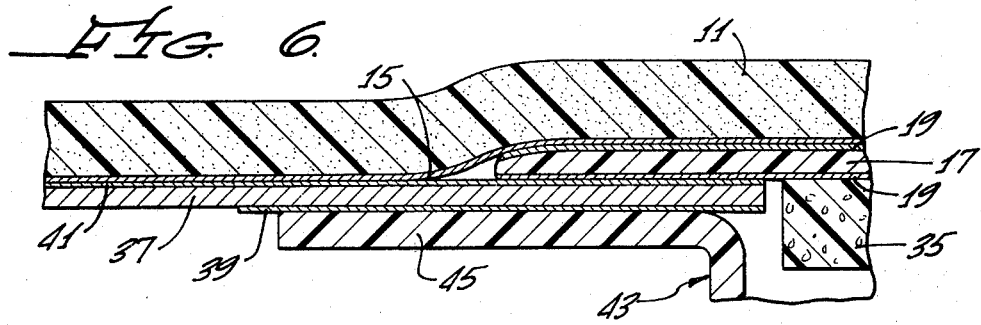
FIG. 6 is an enlarged sectional view showing a portion of the sectional view of FIG. 4.

As particularly shown in FIG. 6, the electrode body member 11 is coated on one entire face by an adhesive 15. The adhesive 15 is selected to provide an adequate bond between the member 11 and the skin of the patient and may be any of a variety of materials commonly used to affix electrodes or bandages to the skin of patients.

Attached to one face of the adhesive coated member 11 by adhesive 15 is a moisture and liquid vapor barrier sheet 17. This sheet 17 is typically constructed as a disc of polyethylene sheet material, latex rubber sheet, or other moisture impervious material which is rendered flexible by being relatively thin. The flexibility of the liquid vapor barrier sheet 17 may therefore be selected by varying the thickness of this sheet 17 to provide electrodes 13 in which the rigidity of the center portion can be selectively increased to provide a more stable center of the electrode as well as a more rigid attachment area for the snap connectors 25 and 27, dependent on the particular application for the electrode 13.

As particularly shown in FIG. 6, both flat faces of the liquid vapor barrier member 17 are preferably coated with an adhesive 19. The adhesive layer 19 adjacent the adhesive coated body member 11 assures a firm contact with the member 11, while the layer 19 opposite the body member 11 is used to bind the liquid vapor barrier member 17 to other elements, as described below. It will be understood that the liquid vapor barrier member 17 is extremely important in that it permits a variety of liquid absorbent or liquid impervious materials for the body member 11 while still insuring an adequate seal for the electrolyte within the electrode 13 prior to use.

The adhesive coated member 11 and liquid vapor barrier member 17 are each perforated, the liquid vapor barrier member having a central aperture 21 and the member pad 11 having a central aperture 23. These apertures 21 and 23 are aligned during assembly when the body member 11 and liquid vapor barrier member 17 are joined by their adhesive surfaces 15 and 19. A male snap connector 25, as is commonly utilized with medical electrodes, is then placed on the combination of members 11 and 17. The snap connector 25 is applied to the electrode 13 in two pieces. A base portion 27 includes a circular flange and a central upstanding post 29, typically formed as a unitary construction. An external portion 31 includes a flat disc member formed unitarily with a stud member 33 which has a configuration adapted to interconnect with a female snap fastener. Such female snap fasteners are connected via wires to monitoring equipment, e.g. an ECG monitor. During assembly, the base portion 27 is applied to the adhesive layer 19 of the liquid vapor barrier member 17 with the upstanding post member 29 passing through the liquid vapor barrier member 17 and the body member 11. The external portion 31 is then placed over the upstanding post 29 and crimped onto the post 29 to rigidly interconnect the base portion 27 and external portion 31 in the common fashion. The adhesive interconnection between the adhesive layer 19 of the liquid vapor barrier member 17 and the circular flange of the base portion 27 of the snap fastener 25 forms a continuous impermeable covering beneath the body member 11 which is important for long-term storage and use of the electrode 13.

A liquid absorbent sponge pad 35, typically in the form of a disc, is attached to the adhesive layer 19 on the liquid vapor barrier member 17 and completely covers the base portion 27 of the snap fastener 25. This foam pad 35 is formed of liquid absorbent material, typically foamed polyurethane, which permits an electrical connection, by means of electrolyte impregnated into the sponge member 35, between the snap fastener 25 and the skin of the patient. The sponge member 35 is preferably applied to the lower adhesive surface 19 of the liquid vapor barrier member 17 prior to impregnation with electrolyte so that the electrolyte will not interfere with an adhesive bond between these members. Electrolyte is then applied to the sponge member 35 so that it impregnates the sponge member 35 and contacts the lower member 27 of the snap fastener 25 to complete the electrical circuit. The electrolyte impregnated into the sponge member 35 may be any of a variety of commercially available electrolyte pastes and gels commonly used in medical electrodes.

Figure 3:
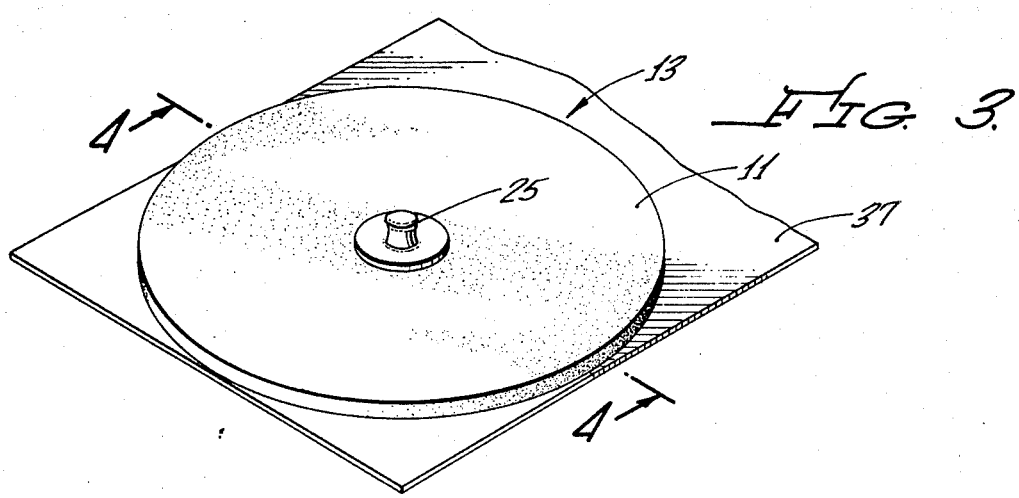
FIG. 3 is a perspective view of the assembled electrode of the present invention during storage.

A carrier sheet 37 is attached to the body member 11 and liquid vapor barrier member 17 by the adhesive layers 15 and 19. The carrier sheet 37 is advantageously manufactured of a moisture and liquid vapor barrier material. A very useful material is a synthetic paper material formed as a multi-ply sheet of polypropylene containing additives and fillers sold by Kimberly Clark Company under the trademark KIMDURA. This material has been found to provide excellent moisture and vapor impermeability. The carrier sheet 37, as shown in FIG. 3, forms a substrate on which multiple electrodes 13 may be transported and stored. Typically, a single carrier sheet 37 connects three electrodes 13 but may also be used to affix a single electrode or any number thereof. The carrier sheet 37 includes an enlarged aperture 39 for each electrode 13 and, as specifically shown in FIGS. 1 and 4, this aperture is circular and has a diameter slightly larger than the diameter of the sponge member 35. Thus, the carrier sheet 37 may be applied to the liquid vapor barrier member 17 and adhesive coated member 11 surrounding the sponge member 35. As specifically shown in FIG. 6, the lower surface of the carrier member 37, at least in an annular ring surrounding the sponge member 35, includes a coating of heat sealable material 39. This material, for example, may be polyvinylchloride, and is designed to melt at a predetermined sealing temperature. The upper surface of the carrier sheet 37, as viewed in FIG. 6, is coated with a layer of liquid silicon coating 41. Such liquid silicon coating 41 is commonly used with pressure sensitive adhesives to permit easy removal of the adhesive element from a carrier member. Thus, the liquid silicon coating 41 on the carrier member 47 allows removal of the body member 11 and liquid vapor barrier member 17 from the carrier member 37 without risk of damaging the body member 11 or the adhesive layers 19.

Figure 4:
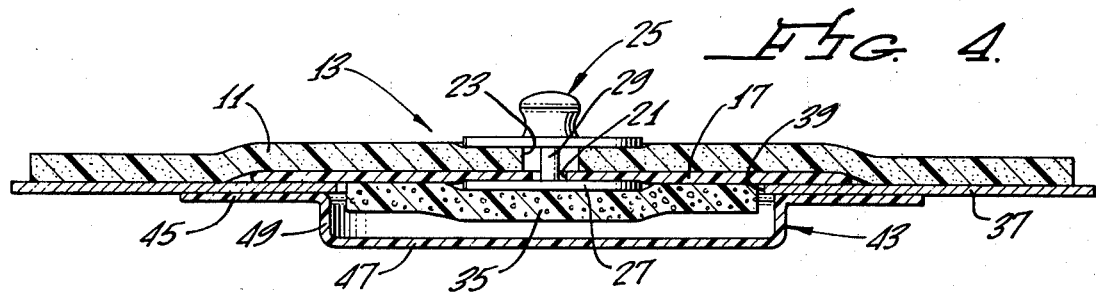
FIG. 4 is a sectional view taken along lines 4—4 of FIG. 3 showing the elements of the embodiment of FIG. 1 during storage.

Adjacent each of the electrodes 13 on the carrier strip 37 is a cup member 43 formed of a heat sealable material such as polyvinylchloride. This member 43, as particularly shown in FIGS. 1 and 5, includes an annular flange 45 surrounding and unitary with a depending cup portion including a planar bottom wall 47 and a cylindrical or slightly conical side wall 49. The flange 45 is placed around the sponge member 35 as shown in FIG. 4 and the entire electrode assembly is placed under pressure between a tool (not shown) and a heated annular mandrel 51, the tool pressing against the body member 11 and the heated mandrel 51 pressing against the flange 45 of the cup member 43. This annular mandrel 51 is heated to a temperature designed to melt the heat sealing flange 45 and heat sealing layer 39 on the carrier sheet 37 so that, with the application of heat and pressure, the mandrel 51 forms an extremely vapor and moisture impervious seal between the cup member 43 and carrier sheet 37 and reinforces the seal between the vapor barrier number 17, the adhesive layer 16 and 19 and the carrier sheet 37.

It can be seen from this first embodiment that the sponge member 35 and its impregnated electrolyte is surrounded during storage by a completely impervious container comprising the snap fastener 25, the liquid vapor barrier member 17, the carrier sheet 37 and the cup member 43, each bonded together to form a moisture and liquid vapor barrier interface. This overall combination provides an electrode 13 which may be stored indefinitely prior to use without fear of loss of the electrolyte paste or gel which would render the electrode 13 unless and without the use of any outer foil container. At the same time, this impervious enclosure for the sponge member 35 assures the cleanliness of the device which is to be applied to the patient without the incorporation of rigid materials which would make the electrode 13 uncomfortable to wear for extended periods.

When the electrode 13 is to be used, the edge of the adhesive coated body member 11 is grasped and the member 11 is pulled from the carrier strip 37, lifting the liquid vapor barrier sheet 17 and sponge member 35 along with the snap fastener 25 from the carrier sheet, leaving the carrier sheet 37 and cup member 43 which may be discarded. The electrode 13 is then applied to the patient by attaching the adhesive coated member 11 and liquid vapor barrier member 17 to the skin of the patient by means of the adhesive layers 15 and 19. During use, the liquid vapor barrier member 17, which is adhesively attached to the skin of the patient, prevents migration of the electrolyte to an area between the body member 11 and the skin of the patient which might, over extended usage, degrade the adhesive layer 15 and allow accidental removal of the electrode 13 from the patient's skin. At the same time, this liquid vapor barrier member 17 restricts the electrical cottact area to approximately the dimensions of the sponge member 35 so that the electrolyte contact area does not change during extended periods of use. A female snap connector is attached to the snap fastener 25 and includes a sensing wire which is normally connected via a patient cable to the monitoring equipment which monitors the electrical activity of the heart.

Figure 5:
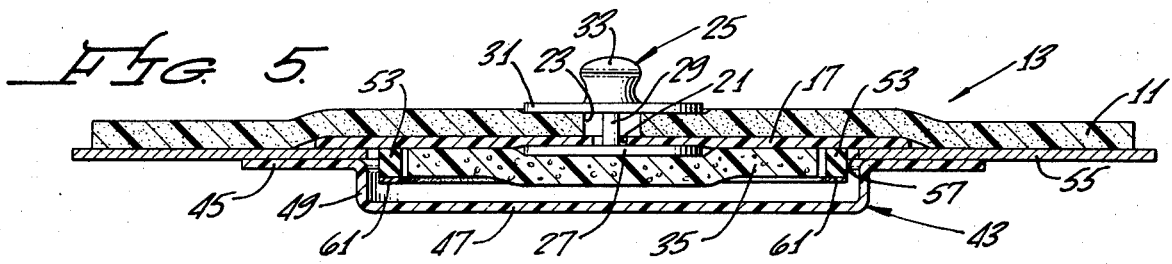
FIG. 5 is a sectional view taken along lines 4—4 of FIG. 3 showing the elements of the alternate embodiment of FIG. 2 of the present invention.

Referring now to FIGS. 2, 3, 5 and 7, an alternate embodiment of the present invention will be disclosed. It should be noted that the overall appearance in the perspective view of FIG. 3 is identical for each of the embodiments of the present invention. In the disclosure of this alternate embodiment, those parts which are identical in construction to the embodiment of FIGS. 1, 3, 4 and 6 are numbered identically in the drawings and their operation and construction are identical to the previous disclosure. In addition to the elements in the first embodiment, this second embodiment includes a soft, pliable, elastomeric annular retaining ring 53 which acts as a gel collar for maintaining the electrolyte paste or gel in the sponge 35 to a confined area during use of the apparatus, without discomfort to the patient. As shown in FIG. 5, the axial height of ring 53 is advantageously the same distance or slightly larger than the thickness of sponge 35. It will be recognized that the carrier sheet 55 of this embodiment includes an enlarged diameter aperture 57 to surround the annular retaining ring 53. This permits the retaining ring 53 to be attached directly to the adhesive layer 19 on the lower surface, as viewed in FIG. 5, of the liquid vapor barrier member 17. The retaining ring 53 is preferably constructed of a soft, liquid impervious material such as polyethylene foam, latex foam or foam rubber, each of which will provide a moisture and vapor barrier while remaining extremely resilient and soft to the touch. As can be seen in FIG. 5, the retaining ring 53 does not interfere with the sealed enclosure for the sponge 35 which was described above in reference to the first embodiment.

Figure 1:
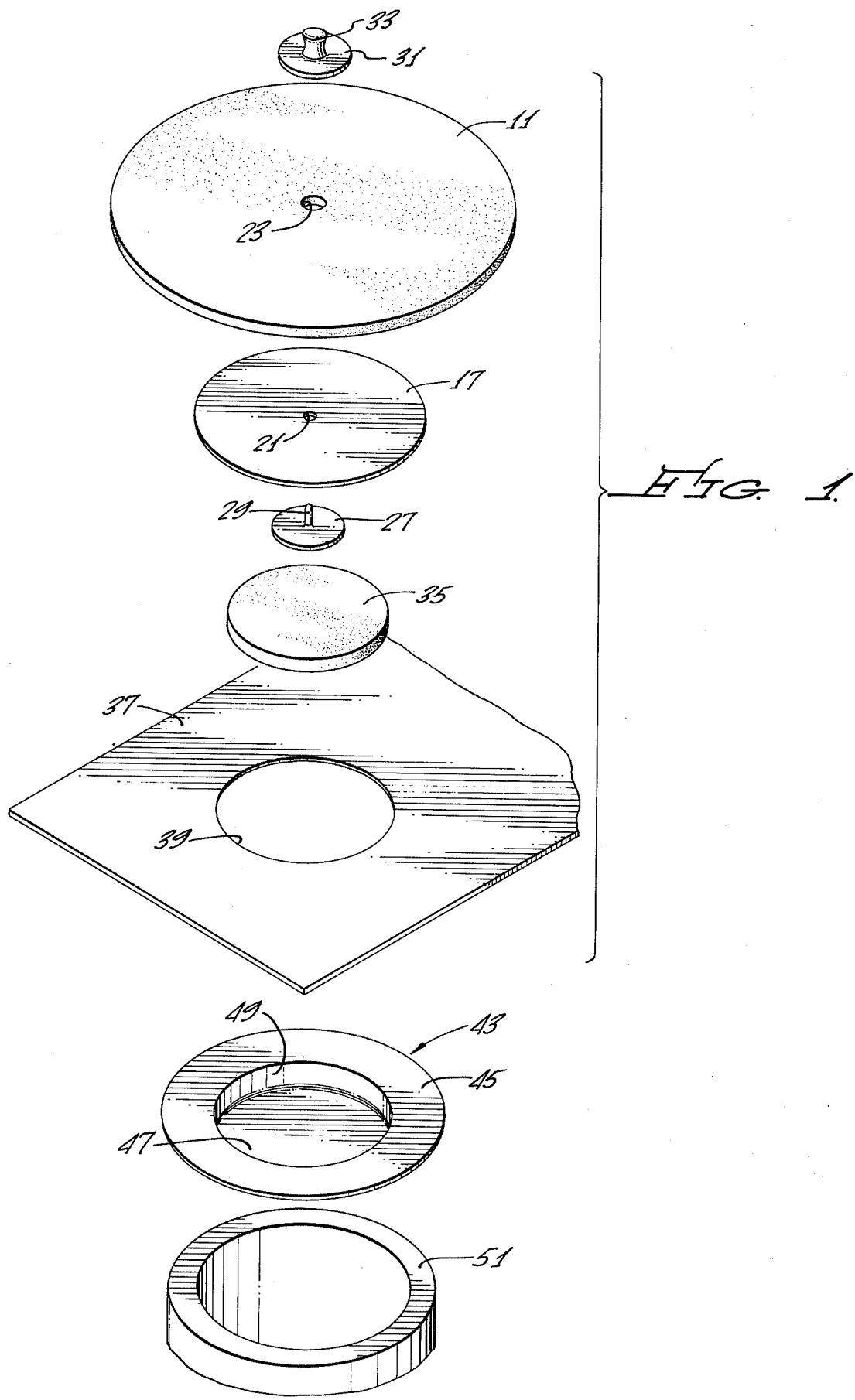
FIG. 1 is an exploded perspective view of the medical electrode of the present invention and a heat sealing mandrel used to fabricate the electrode.
Figure 2:
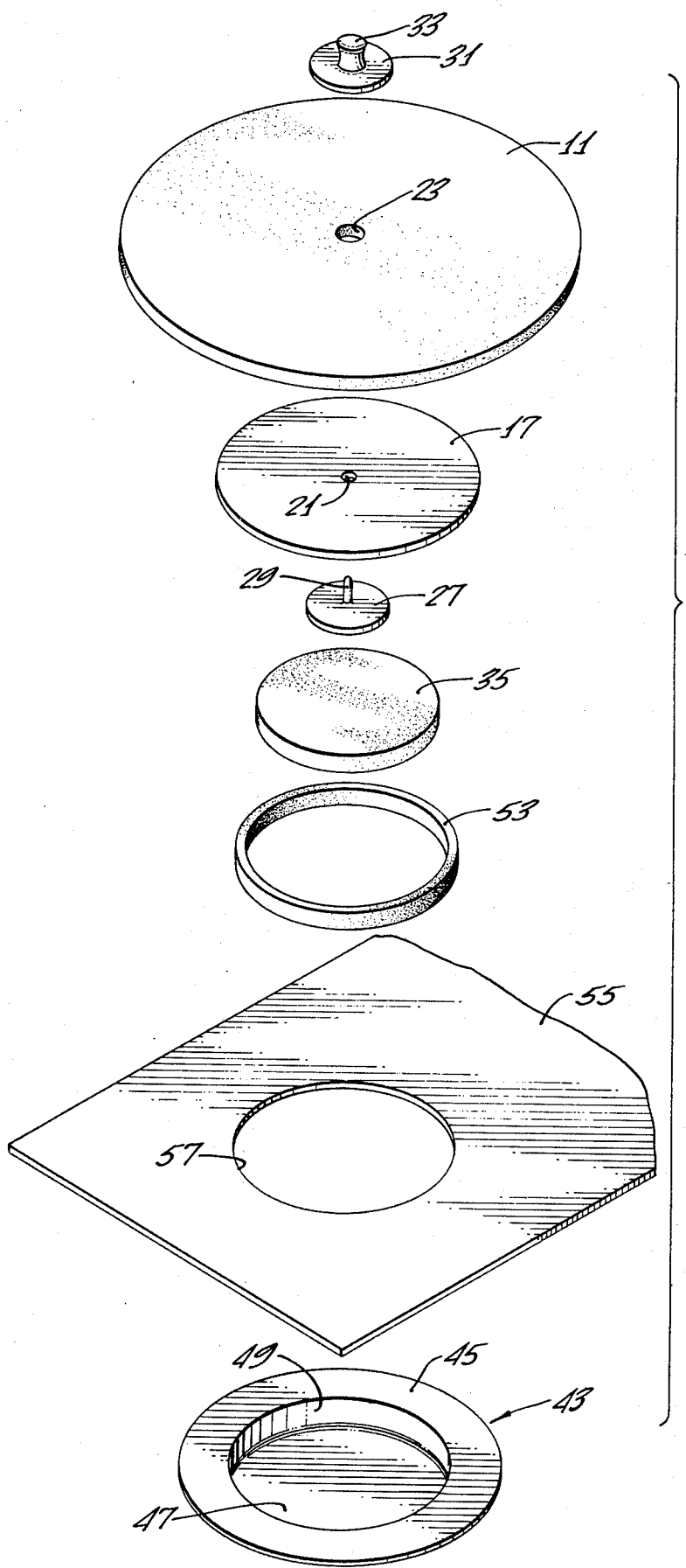
FIG. 2 is an exploded perspective view of an alternate embodiment of the medical electrode of the present invention.

In the same manner as described for the embodiment of FIGS. 1 and 4, the rigidity of sheet 17 may be selected to provide a more stable center of the electrode and thus a more rigid attachment area for the annular retaining ring 53. This will result in reduced noise artifacts and therefore provide superior performance of the electrode.

Figure 7:
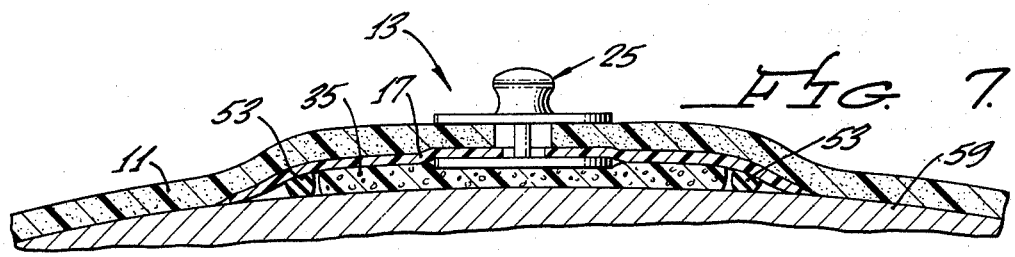
FIG. 7 is a sectional view similar to the sectional view of FIG. 5 showing the alternate embodiment of FIG. 2 after attachment to the skin of a patient.

Application of the second embodiment to the skin 59 of a patient is shown in FIG. 7. The adhesive layers 15 and 19 on the adhesive pad 11 and liquid vapor barrier member 17, respectively, draw the adhesive coated body member 11 and liquid vapor barrier member 17 tightly against the skin 59 of the patient. This, in turn, tends to compress the annular ring 53 against the skin 59 of the patient so that the ring 53 forms a collar surrounding the gel-impregnated sponge 35, preventing migration of the electrolyte paste or gel outside of the ring 53. The resilience of the member 53 assures that the device will be comfortable against the skin 59 of the patient and additionally assures a continuous contact between the annular ring 53 and the skin 59 of the patient throughout the perimeter surrounding the sponge member 35, even though the skin 59 of the patient is bent or stretched, so that the electrolyte is always maintained within the confines of the ring 53. To further ensure the restriction of electrolyte to this area, the lower surface of the retaining ring 53, as viewed in FIG. 5, is advantageously coated with adhesive 61. This adhesive 61 does not contact the cup member 43 during storage, but seals the retaining ring 53 to the skin 59 of the patient during use.

The confinement of the electrolyte within the retaining ring 53 assures that the adhesive layers 15 and 19 on the body member 11 and liquid vapor barrier member 17, respectively, will not be impaired by the presence of electrolyte, and also assures that a uniform contact area will be maintained between the electrolyte and the skin 59 of the patient throughout extended use. It will be understood that, both prior to use and during use, the adhesive layer 19 on the liquid vapor barrier member 17 supports and maintains the position of the retaining ring 53 so that the ring 53 cannot shift relative the skin 59 of the patient or the remainder of the electrode 25.

What is claimed is:

1. A medical electrode, comprising:
    a thin, flexible body member coated with adhesive on one side for adhesion to the skin of a patient and including a central aperture;
    a thin flexible barrier sheet attached to said adhesive coating on said flexible body member, said sheet being impervious to moisture and liquid vapor and having a central aperture aligned with said body member aperture, the area of said sheet being smaller than the area of said body member to provide an exposed perimeter area of said body member surrounding said sheet in all directions;
    an electrically conductive snap fastener passing through said body member aperture and said barrier sheet aperture, said fastener including an enlarged flange, said barrier sheet having a surface opposite said flexible body member abutting said enlarged flange to seal said aperture in said barrier sheet;
    a thin carrier sheet formed of moisture impervious material attached to said body member adhesive, said carrier sheet having an aperture;
    a liquid absorbent sponge member positioned against said enlarged flange of said snap fastener, said sponge member positioned within said aperture of said carrier sheet;
    an electrolyte material impregnated within said sponge member; and
    a vapor and moisture impervious cup member surrounding one side of said sponge member to enclose said sponge member between said cup member and said barrier sheet, said cup member including an annular flange attached to one surface of said carrier sheet.

2. A medical electrode as defined in claim 1 additionally comprising:
    an adhesive coating on the surface of said moisture and liquid vapor barrier sheet opposite said flexible body member, said barrier sheet adhesive coating being attached to said thin carrier sheet and said liquid absorbent sponge member.

3. A medical electrode as defined in claim 2 additionally comprising:
    an adhesive coating on the side of said moisture and liquid vapor barrier sheet adjacent said flexible body member attaching said barrier sheet to said body member.

4. A medical electrode as defined in claim 1 additionally comprising:
    means for sealing said annular flange of said cup member to said carrier sheet.

5. A medical electrode as defined in claim 4 wherein said means for sealing comprises:
    a coating on said one surface of said thin carrier sheet, said coating having a predetermined melting temperature for heat sealing purposes; and means on said annular flange of said cup member melting at said predetermined temperature for heat sealing to said coating on said thin carrier sheet.

6. A medical electrode as defined in claim 5 wherein said entire cup member including said annular flange is formed of material which melts at said predetermined temperature.

7. A medical electrode as defined in claim 1 wherein said thin carrier sheet is formed of polymeric material.

8. A medical electrode, comprising:
a flat electrode body member having an adhesive coating on one side;

a thin, flexible barrier sheet member impervious to moisture and liquid vapor, said barrier sheet having a surface area smaller than the surface area of said one side of said body member, said barrier sheet member attached to said adhesive coating;
an electrically conductive contact member passing through said body member and said barrier sheet member to provide an electrical terminal adjacent said barrier sheet member;
a liquid absorbent sponge member attached to said barrier sheet member and covering said electrical terminal; and
an electrolyte impregnated within said liquid absorbent sponge member in contact with said electrical terminal for contact to the skin of a patient.

9. A medical electrode as defined in claim 8 wherein said moisture and liquid vapor barrier sheet member is formed of polyethylene.

10. A medical electrode as defined in claim 8 additionally comprising:
means surrounding one side of said liquid absorbent sponge member opposite said barrier sheet member and sealed to said barrier sheet member for prohibiting evaporation and migration of said electrolyte during storage of said medical electrode.

11. A medical electrode as defined in claim 10 wherein said means for prohibiting migration and evaporation comprises:

an impervious carrier sheet attached to said flat electrode body member and including an aperture receiving said liquid absorbent sponge member; and
a cup member surrounding one side of said liquid absorbent sponge member to enclose said sponge member between said cup member and said barrier sheet member, said cup member melted into said impervious carrier sheet.

12. A medical electrode as defined in claim 8 wherein rigidity is imparted to the portion underlying said liquid absorbent sponge member by selecting a barrier sheet member having a predetermined flexibility.

13. A disposable pre-gelled medical electrode which has a long shelf life without the use of an outer foil container or like multiple packaging technique comprising:
an adhesive coated sheet for application to the skin of a patient;
an electrical terminal passing through said sheet;
an electrolyte impregnated sponge member in contact with said electrical terminal for contact with the skin of a patient;
a carrier sheet formed of polymeric material and attached to said adhesive coated sheet for protecting said adhesive coated sheet prior to application to the skin of a patient;
a coating on one surface of said carrier sheet, said coating having a predetermined melting temperature for heat sealing purposes; and
a vapor and moisture impervious cup member surrounding one side of said sponge member to enclose said sponge member between said cup member and said adhesive coated sheet, said cup member including an annular flange attached to said one surface of said carrier sheet melting at said predetermined temperature for heat sealing to said coating on said carrier sheet.

14. The disposable pre-gelled medical electrode as defined in claim 13 wherein said carrier sheet is formed of a multi-ply sheet of polypropylene containing additives and fillers such as KIMDURA synthetic paper.

* * * * *